(12) United States Patent
Tripp et al.

(10) Patent No.: US 6,186,960 B1
(45) Date of Patent: Feb. 13, 2001

(54) DISPOSABLE MEDICAL COLLECTION TUBE HOLDER WITH RETRACTABLE NEEDLE

(75) Inventors: Martha J. Tripp, Houston; Joseph J. Janecka, Jr., Richmond, both of TX (US)

(73) Assignee: Texas Applied Biomedical Services, Inc., Houston, TX (US)

( * ) Notice: Under 35 U.S.C. 154(b), the term of this patent shall be extended for 0 days.

(21) Appl. No.: 09/175,484

(22) Filed: Oct. 20, 1998

(51) Int. Cl.[7] .................................................. A61B 5/00
(52) U.S. Cl. ......................... 600/576; 604/110; 604/195
(58) Field of Search .................................. 600/575, 576, 600/573, 578, 579; 604/110, 195, 187, 192, 197, 198, 220, 225, 226, 263

(56) References Cited

U.S. PATENT DOCUMENTS

| | | | |
|---|---|---|---|
| 3,008,570 | 11/1961 | Roehr et al. | 206/43 |
| 3,107,785 | 10/1963 | Roehr | 206/63.2 |
| 3,895,633 | 7/1975 | Bartner et al. | 128/218 DA |
| 3,976,069 | 8/1976 | Ong | 128/218 D |
| 4,296,759 | * 10/1981 | Joslin et al. | 600/579 |
| 4,300,678 | 11/1981 | Gyure et al. | 203/364 |
| 4,356,822 | 11/1982 | Winstead-Hall | 128/215 |
| 4,425,120 | 1/1984 | Sampson et al. | 604/198 |
| 4,592,744 | 6/1986 | Jagger et al. | 604/192 |
| 4,639,249 | 1/1987 | Larson | 604/198 |
| 4,655,751 | 4/1987 | Harbaugh | 604/198 |
| 4,666,435 | 5/1987 | Braginetz | 604/198 |
| 4,723,943 | 2/1988 | Spencer | 604/198 |
| 4,738,663 | 4/1988 | Bogan | 604/198 |
| 4,747,830 | 5/1988 | Gloyer et al. | 604/110 |
| 4,790,822 | 12/1988 | Haining | 604/110 |
| 4,816,022 | 3/1989 | Poncy | 604/198 |
| 4,826,483 | 5/1989 | Molnar, IV | 604/110 |
| 5,000,736 | 3/1991 | Kaufhold, Jr. et al. | 604/110 |
| 5,125,898 | 6/1992 | Kaufhold, Jr. et al. | 604/110 |
| 5,217,025 | * 6/1993 | Okamura | 600/578 |
| 5,337,756 | * 8/1994 | Barbier et al. | 600/576 |
| 5,860,937 | * 1/1999 | Cohen | 600/576 |

* cited by examiner

Primary Examiner—Cary O'Connor
Assistant Examiner—Pamela Wingood
(74) Attorney, Agent, or Firm—Jackie Lee Duke

(57) ABSTRACT

A disposable medical collection tube holder assembly with retractable needle is disclosed. The spent needle, or other similar medical device, affixed to the holder may be safely encapsulated and disposed by a simple, one handed operation, and, both the needle and the holder are rendered useless for any subsequent operation. The invention is comprised of two parts, a collection tube holder and an evacuated accessory fitted with an air release/vacuum seal mechanism that readily permits the introduction of the vacuum into the hollow chamber of the accessory. When using the collection tube holder in the standard manner, and after the collection of the blood or other bodily fluids is complete, the collection test tube is withdrawn from the holder and then the needle withdrawn from the vein. The accessory, a tubular member with an evacuated interior, is inserted into the collection tube holder fully, and longitudinally axial force is applied to the proximal (thumb) end of the evacuated accessory. This causes a sequence of events that results in encapsulation of the spent needle within the interior of the accessory. The entire assembly may now be safely disposed.

10 Claims, 7 Drawing Sheets

DISPOSABLE MEDICAL COLLECTION TUBE HOLDER WITH RETRACTABLE NEEDLE

BACKGROUND OF THE INVENTION

1. Field of the Invention

This invention relates generally to medical instruments, and more particularly to a specialized medical test tube holder assembly that is used in the collection of blood or other body fluids via evacuated test tubes. Still more particularly, the present invention relates firstly to a disposable article, a medical test tube holder with modifications that permit an attached needle or other medical sharps device to be quickly and safely detached from the holder after use, and secondly, to an accessory article, an evacuated chamber that captures the detached needle and retracts it into the chamber, all actions being accomplished in a safe manner with one hand. The disposable medical test tube holder assembly of the present invention is fitted with a detachable needle port hub and a wedging hub release ring that positions the detachable needle port hub within the interior wall of the holder at the distal (towards the needle) end of the holder. The detachable needle port hub of the holder may have the needle pre-molded into the hub as an integral component of the holder or, as in the preferred embodiment, may be a needle hub interface that is compliant for use with specialized needle devices or other similar medical devices, The disposable holder may be of any particular shape to accomplish a specific purpose or, as in the preferred embodiment, may be of a generally tubular shape with varying interior diameter from proximal end to distal end with flanges fitted on the proximal end to assist the operator to hold the device during use. The evacuated accessory consists of a hollow chamber fitted with a specialized combination part mounted on the distal end of the evacuated accessory. The specialized combination part contains a needle port hub capturing device; it has an air release/vacuum seal mechanism to readily introduce and hold a pressure differential within the hollow chamber of the evacuated accessory; and, it has gasket seals which maintain a pressure differential between the hollow chamber of the evacuated accessory and the atmosphere. The hollow chamber of the evacuated accessory may be constructed in the form of a test tube, false plunger or other chamber of appropriate size, shape and density capable of holding and maintaining a pressure differential when fitted with a specialized combination part. The specialized combination part functions to capture a detachable target contrivance, allows introduction of a pressure differential within the hollow chamber, and seals the pressure differential between the hollow chamber and the atmosphere.

A problem for doctors, nurses and other health care personnel who use or handle medicinal blood collection devices is the accidental puncture of the skin by the needle. The problem can be very serious if the needle has been used. Potentially fatal diseases, such as hepatitis or Acquired Immune Deficiency Syndrome (AIDS), can be contracted if the needle has been used on an infected subject.

The needle used in the collection of blood or other body fluids is typically covered with a removable sheath prior to and following use to prevent accidental contact, but the act of replacing the sheath after use can still result in accidental skin puncture. Also, if the sheath is not securely repositioned, the danger exists that personnel subsequently involved in disposal of the device may become infected by accidental puncture.

2. Description of Related Art

U.S. Pat. No. 3,008,570 discloses the use of a removable cap for the purposes of enclosing and protecting a sterilized syringe in a transport.

Solutions that attempt to better protect the health care worker include that disclosed in U.S. Pat. No. 4,790,822. The '822 patent discloses a disposable syringe in which the needle can be first captured by the plunger and then withdrawn into the barrel in a position with the needle completely protected by the barrel. The plunger can then be broken off, leaving the broken end flush with the end of the barrel, so that the needle cannot be accidentally pushed out from the barrel and exposed.

U.S. Pat. No. 4,747,830 discloses a similar system with a plunger that can be broken off once the needle is retracted into the barrel. U.S. Pat. Nos. 4,692,156 and 4,643,200 disclose similar systems, used with a blood donor assembly, which allows retraction of a needle into a barrel.

U.S. Pat. No. 4,425,120 discloses a needle guard movable on the syringe barrel between an extended position in which the needle guard shields the needle and a retracted position in which the needle is exposed for use.

U.S. Pat. No. 4,816,022 discloses a syringe with a sliding cap for preventing accidental puncture. The '022 patent utilizes a nub and backseat for engagement of a nose-piece for securing the cap around the syringe for safety purposes. U.S. Pat. No. 4,840,619 discloses a syringe assembly that has a transport held in telescoping position over a syringe by flanges. Other and various means of sheathing or shielding a syringe are shown in the following U.S. Pat. Nos.: 4,738,663; 4,723,943; 4,666,435; 4,655,751; 4,639,249; 4,592,744; 4,356,822; 4,300,678; 3,976,069; 3,895,633; 3,107,785.

U.S. Pat. Nos. 4,826,483 discloses a non-reusable syringe with one-way movable position.

U.S. Pat. Nos. 5,000,736 and 5,125,898 to Kaufhold et al show disposable syringes with automatic needle retraction. The Kaufhold patents allow the used needle or other medical sharps device to be encapsulated within an evacuated plunger of the syringe and be rendered safe for handling immediately after use and throughout subsequent disposal procedures, as well as rendering the syringe unsuitable for further use. The Kaufhold patents do not address the safety issues associated with disposal of needles or other medical sharps devices when used with those specialized blood collection devices that do not have and do not use plungers as part of normal operation.

SUMMARY OF THE INVENTION

This invention relates to a disposable medical collection tube holder with retractable needle designed for use in blood and other body fluid collection procedures. The first article of the present invention includes a collection tube holder similar to that sold under the Vacutainer™ trademark. The collection tube holder is a tubular member with a proximal end and a distal end. The distal end (towards the needle) is fitted with an orifice that surrounds a detachable needle port hub; the needle port hub in turn accepts a bi-directional needle, or other similar medical sharps device, used in the collection of blood or other body fluids. The detachable needle port hub is secured within the interior of the collection tube holder at the distal end by a hub release ring that is wedged between the detachable needle port hub and the interior wall of the holder. An annular channel is also molded into the distal end of the collection tube holder. At the time of detachment of the needle port hub and affixed needle, the hub release ring will advance into this annular channel. During typical use, the bi-directional needle assembly is secured within the opening of the needle port hub, one needle end is exposed to the exterior environment and the other needle end is contained within the interior of the collection tube holder. The operator skillfully guides and inserts the exterior needle into a subject's vein, then inserts an evacuated test tube into the interior of the collection tube holder and presses the rubber stopper of an evacuated test tube onto the interior needle. The negative pressure in the evacuated test tube causes blood to be collected in the test tube. When the collection of the blood is complete, the test tube is withdrawn from the interior needle and then the exterior needle is withdrawn from the vein. At this point the exterior needle is exposed and individuals are at greatest risk from accidental puncture; the interior needle is shielded within the interior of the holder.

The present invention further includes a second article, an accessory, an appropriately sized evacuated chamber, typically a 16 mm×125 mm test tube, fitted at the distal end (that end that will face the needle) with a specialized combination part. The combination part has an air release/vacuum seal mechanism that permits the introduction and retention of negative pressure within the chamber; has gaskets at the perimeter of the combination part that seal the combination part within the walls of the chamber; and, has an axially extending catch ring feature at the distal end of the combination part that captures the detachable needle port hub with affixed needle at the appropriate time. The air release / vacuum seal mechanism of the combination part contains a central bore therethrough and companion air check device positioned therein. The combination part has resilient gaskets that seal the combination part within the bore of the evacuated chamber. The configuration of the distal portion of the combination part creates a catch ring that is oriented with its outer end sized to grasp the detachable needle port hub at the appropriate time. A retaining ring is securely positioned at the distal end of the combination part and holds the combination part in position within the chamber of the evacuated accessory.

The operator now inserts the evacuated accessory of the present invention into the collection tube holder in the place of an evacuated test tube, pushing it completely into the collection tube holder. Longitudinally axial force applied to the proximal (thumb) end of the evacuated accessory causes the catch ring portion of the combination part to begin to mate with the detachable needle port hub and affixed needle while simultaneously causing the hub release ring holding the needle port hub within the collection tube holder to release from the needle port hub and advance into the channel in the collection tube. Continued longitudinally axial force applied on the proximal end of the evacuated accessory strengthens the mating between the catch ring and the detachable needle port hub, and, causes the retaining ring holding the combination part within the accessory chamber to release and advance into the annular channel. The entire complex formed by the mating of the needle port hub with affixed needle and the catch ring of the combination part are now released to the action of the negative pressure within the evacuated accessory and the complex is drawn into the interior of the evacuated accessory. Both exterior and interior needles are thus encapsulated within the hollow chamber of the evacuated accessory and the entire device may be safely disposed. The collection tube holder is now rendered incapable of future use.

A principal object of the present invention is to provide a disposable medical collection tube holder with retractable needle.

Another object of the present invention is to provide a disposable medical collection tube holder with retractable needle that allows safe disposal of used needles when used with a companion evacuated accessory.

A final object of the present invention is to provide a disposable medical collection tube holder with retractable needle that allows a one handed operation for the safe disposal of used needles when used with the companion evacuated accessory.

These with other objects and advantages of the present invention are pointed out with specificness in the claims annexed hereto and form a part of this disclosure. A full and complete understanding of the invention may be had by reference to the accompanying drawings and description of the preferred embodiments.

BRIEF DESCRIPTION OF THE DRAWINGS

These and other objects and advantages of the present invention are set forth below and further made clear by reference to the drawings, wherein.

DESCRIPTION OF THE PREFERRED EMBODIMENT

Figure 1:
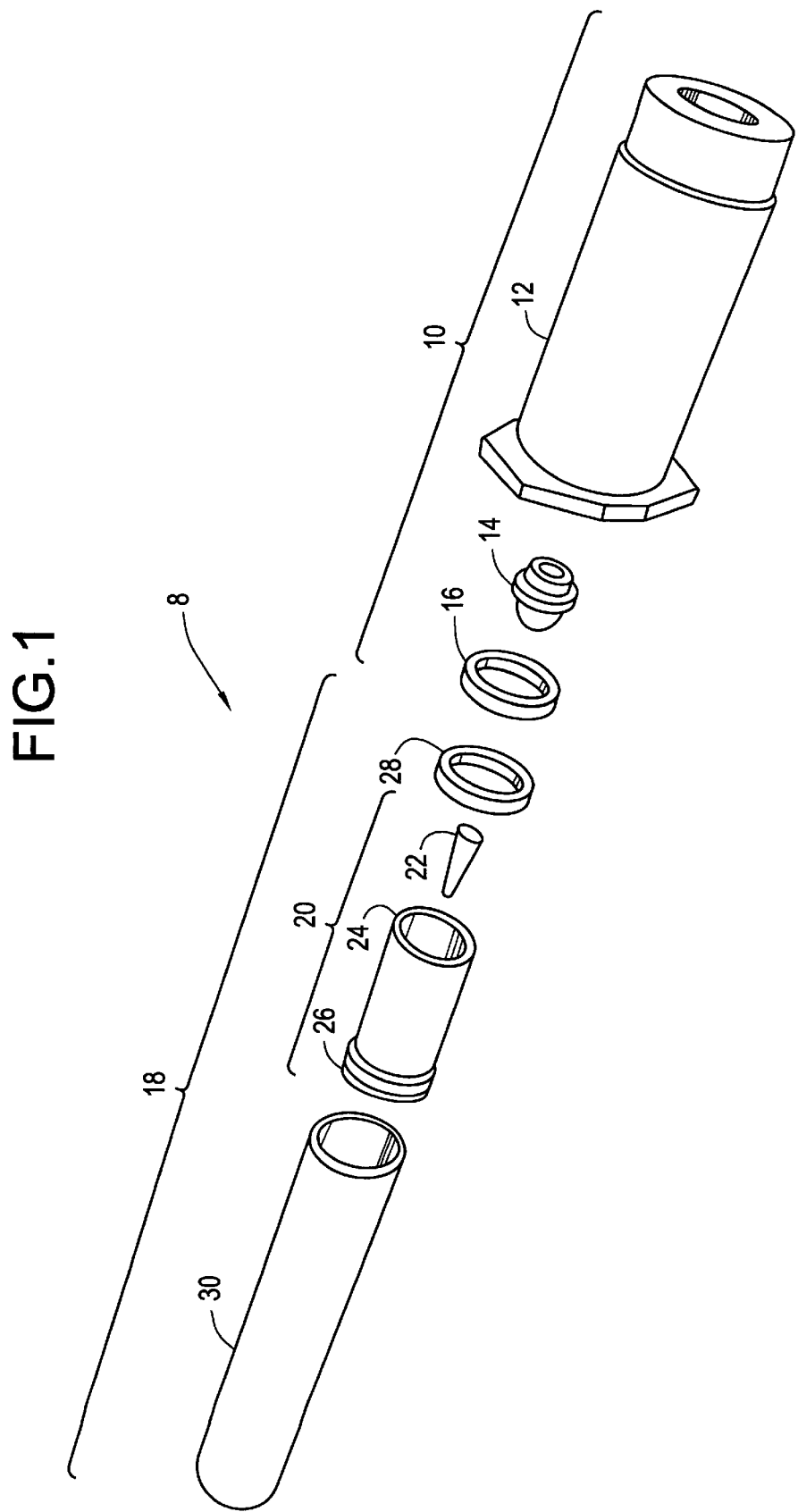
FIG. 1 is an exploded isometric view of the disposable medical collection tube holder and evacuated accessory of the present invention.

With reference to the drawings, and particularly to FIG. 1, disposable medical collection tube holder assembly 8, including disposable medical collection tube holder 10 and evacuated accessory 18 of the present invention are shown in an exploded isometric view. Disposable medical collection tube holder 10 includes collection tube holder body 12, detachable needle port hub 14 and hub release ring 16. Evacuated accessory 18 includes combination part 20, retaining ring 28, and tubular member 30. Combination part 20 contains cone seal or pressure differential seal 22, axially extending catch ring feature 24 and gasket seals 26.

Figure 2:
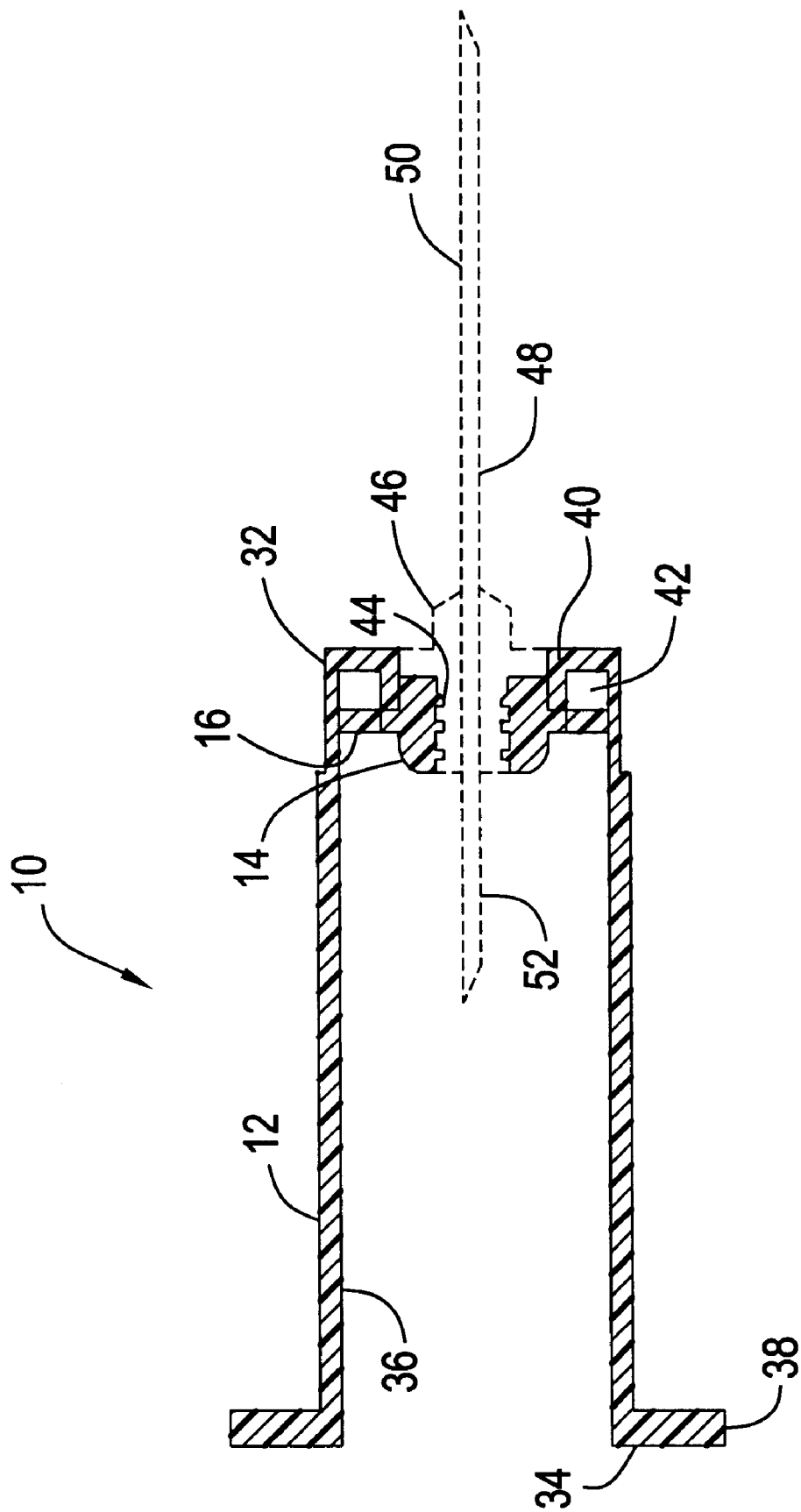
FIG. 2 is a sectional view of the disposable medical collection tube holder with needle installed within the detachable needle port hub.

FIG. 2 is a sectional view of disposable medical collection tube holder 10 with detachable needle port hub 14 and hub release ring 16 shown. Collection tube holder body 12 is a generally tubular member with distal end 32, proximal end 34 and central bore 36. Proximal end 34 has an annularly disposed flange 38 disposed thereon for use as a hand hold by the operator in a manner to be described hereinafter.

Distal end 32 of collection tube holder body 12 has inwardly turned flange 40 formed thereon with annular channel 42 formed therein. Detachable needle port hub 14 is retained within collection tube holder body 12 by hub release ring 16. In this embodiment, the threaded female orifice 44 of detachable needle port hub 14 in turn receives a standard threaded male needle holder 46 with bidirectional needle 48, with exterior needle 50 and interior needle 52, of a configuration well known to those of ordinary skill in the art. At this point disposable medical collection tube holder 10 is configured to be used as a device to collect blood or other body fluids from veins, arteries, or other appropriate physiological sites.

Figure 3:
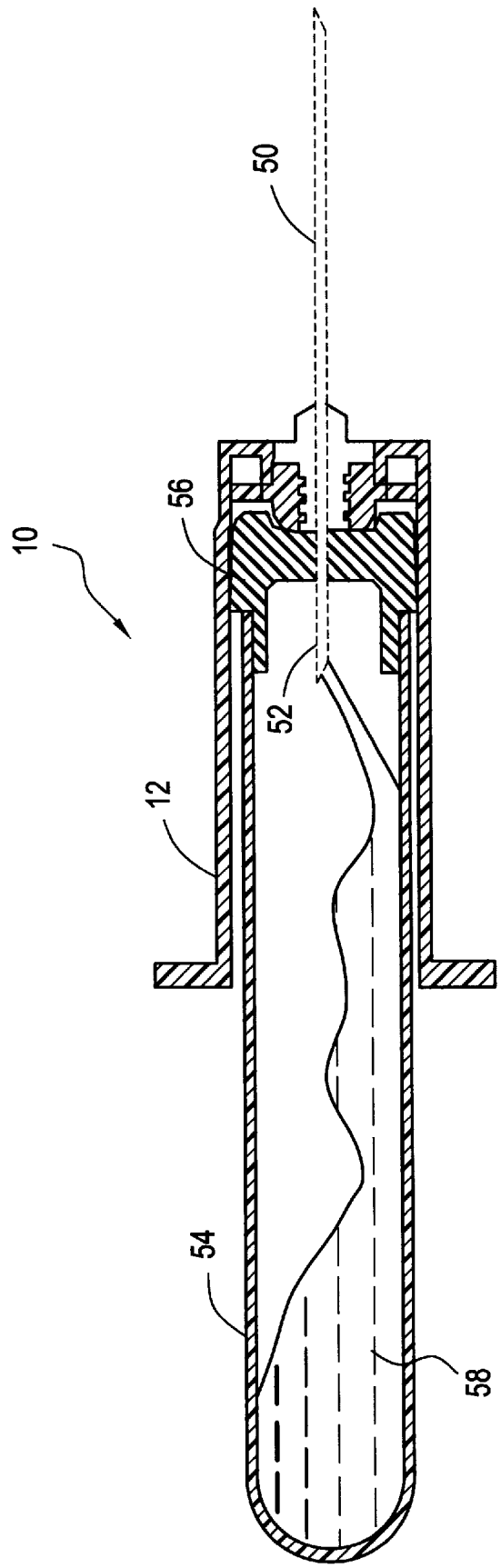
FIG. 3 is a sectional view of the disposable medical collection tube holder with an evacuated blood collection test tube installed.

Referring now to FIG. 3, disposable medical collection tube holder 10 is shown during a typical blood collection procedure. The operator skillfully guides and inserts exterior needle 50 into a subject's vein, then inserts evacuated test tube 54 into the interior of collection tube holder body 12 and presses rubber stopper 56 of evacuated test tube 54 onto interior needle 52. The negative pressure in evacuated test tube 54 causes blood 58 to be collected in evacuated test tube 54. When the collection of blood 58 is complete, evacuated test tube 54 is withdrawn from collection tube holder body 12 and then exterior needle 50 is withdrawn from the vein. At this point exterior needle 50 is exposed and individuals are at greatest risk from accidental puncture; interior needle 52 is shielded within the interior of collection tube holder body 12.

Figure 4:
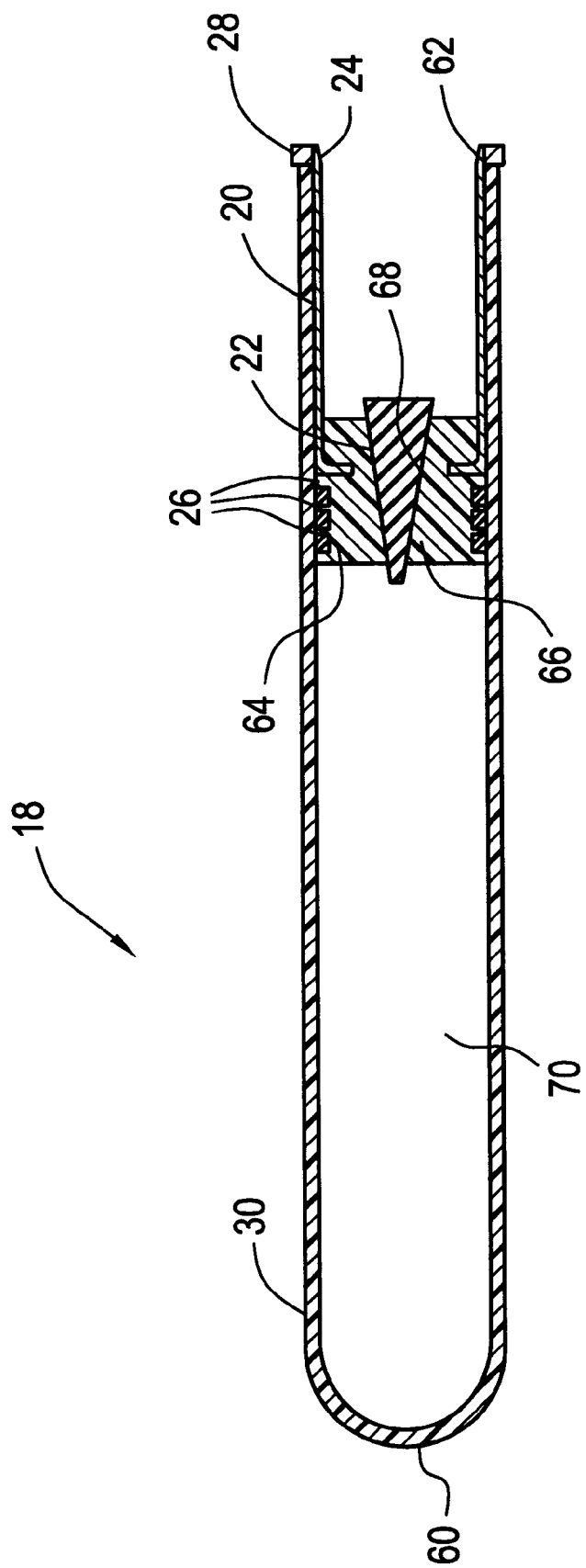
FIG. 4 is a sectional view of the evacuated accessory featuring a combination part that contains a catch ring feature, sealing gaskets and an air release/vacuum seal mechanism.

FIG. 4 is a sectional view of evacuated accessory 18. Accessory 18 is a generally tubular member 30 with closed proximal end 60 and open distal end 62 that is sealed with combination part 20 including cone seal or pressure differential seal 22. Tubular member 30 may be formed of plastic, glass or other suitable material capable of holding a vacuum. Combination part 20 includes an axially extending catch ring 24 and air release/vacuum seal mechanism 66. Seal mechanism 66 includes plug body 64 with central bore 68 therethrough and cone seal or pressure differential seal 22 positioned therein. Gasket seals 26 seal the exterior of plug body against the interior wall of tubular member 30. Combination part 20 is formed by molding plug body 64 of resilient rubber material or other suitable material by processes known to those of ordinary skill in the art, onto the rigid axially extending catch ring 24. Catch ring 24 may be formed of plastic, metal or other suitable rigid material. Combination part 20 is axially movable within tubular member 30 upon release of retaining ring 28 in a manner to be described hereinafter. Evacuated accessory 18 is assembled as combination part 20 is mounted within the open distal end 62 of tubular member 30 with cone seal or pressure differential seal 22 lightly positioned in the central bore 68 of plug body 64 and secured by retaining ring 28. Hollow chamber 70 of evacuated accessory 18 is evacuated by methods known to those of ordinary skill in the art, typically by placing evacuated accessory 18 into an environment of negative pressure wherein the pressure within hollow chamber 70 equalizes with the negative pressure of the environment. Air entrapped within hollow chamber 70 escapes past cone seal or pressure differential seal 22 via central bore 68. When the environment surrounding evacuated accessory 18 is rapidly returned to atmospheric pressure, the equalization of pressure occurring between the environment and evacuated accessory 18, and, between the environment and hollow chamber 70, causes cone seal or pressure differential seal 22 to seat firmly within central bore 68. The negative pressure thus produced within hollow chamber 70 is maintained through the sealing action of gasket seals 26 on the interior walls of tubular member 30 and by cone seal or pressure differential seal 22 within central bore 68. The air release/vacuum seal mechanism 66 may be a design with conical features as shown in the preferred embodiment of central bore 68 and cone seal or pressure differential seal 22, or be a design using a ball within a socket in a channel, or any other configuration that allows the release of air from an enclosed chamber under negative pressure, and, that permits retention of negative pressure when the entire device is rapidly returned to higher pressure. While the catch ring 24 and air release/vacuum seal mechanism 66 are located adjacent to one another and within the distal end of the evacuated accessory 18 in the preferred embodiment, those skilled in the art will note that the two features may be physically separated and still fulfill the objectives of the invention.

Figure 5:
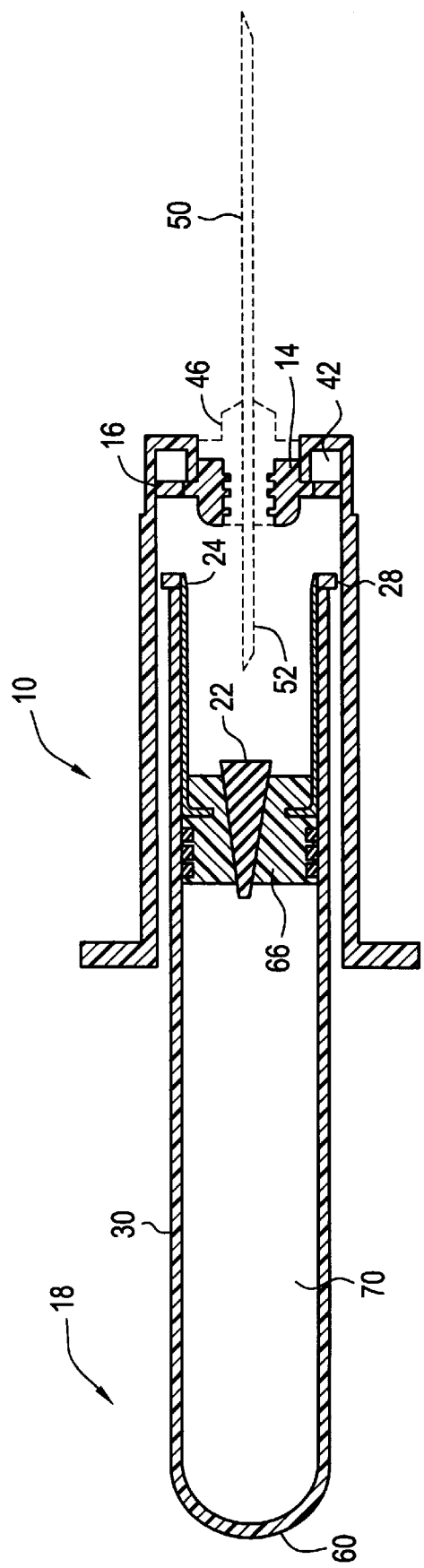
FIG. 5 is a sectional view of the disposable medical collection tube holder with the evacuated accessory partially inserted.

With reference to FIG. 5, evacuated accessory 18 is shown partially inserted into disposable medical collection tube holder 10.

Figure 6:
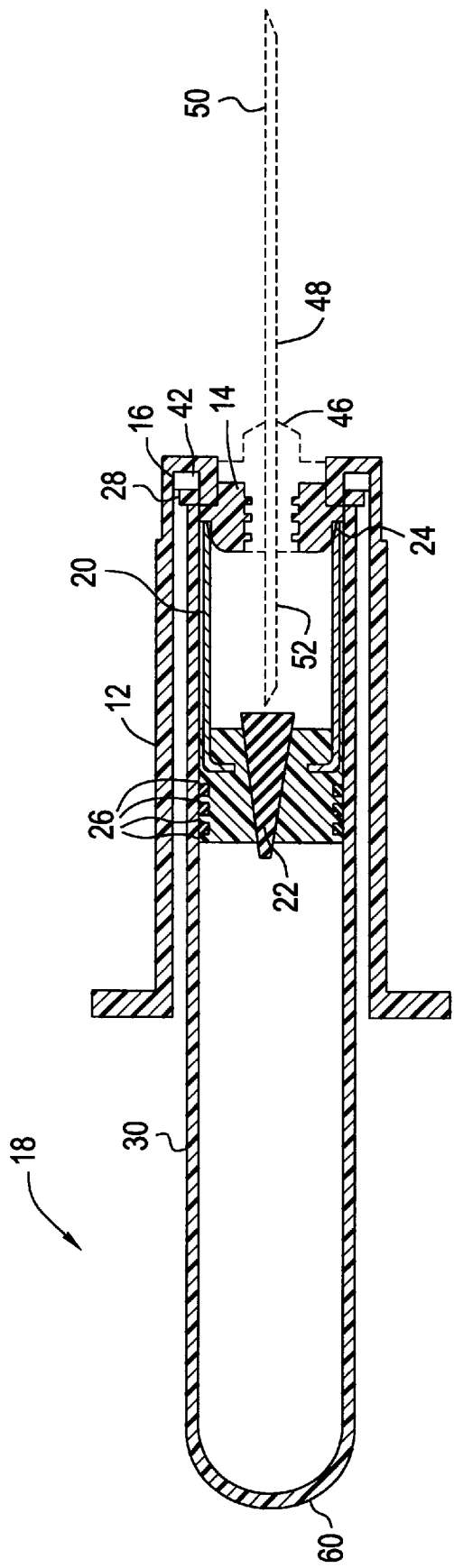
FIG. 6 is a sectional view of the disposable medical collection tube holder with the evacuated accessory fully inserted.
Figure 7:
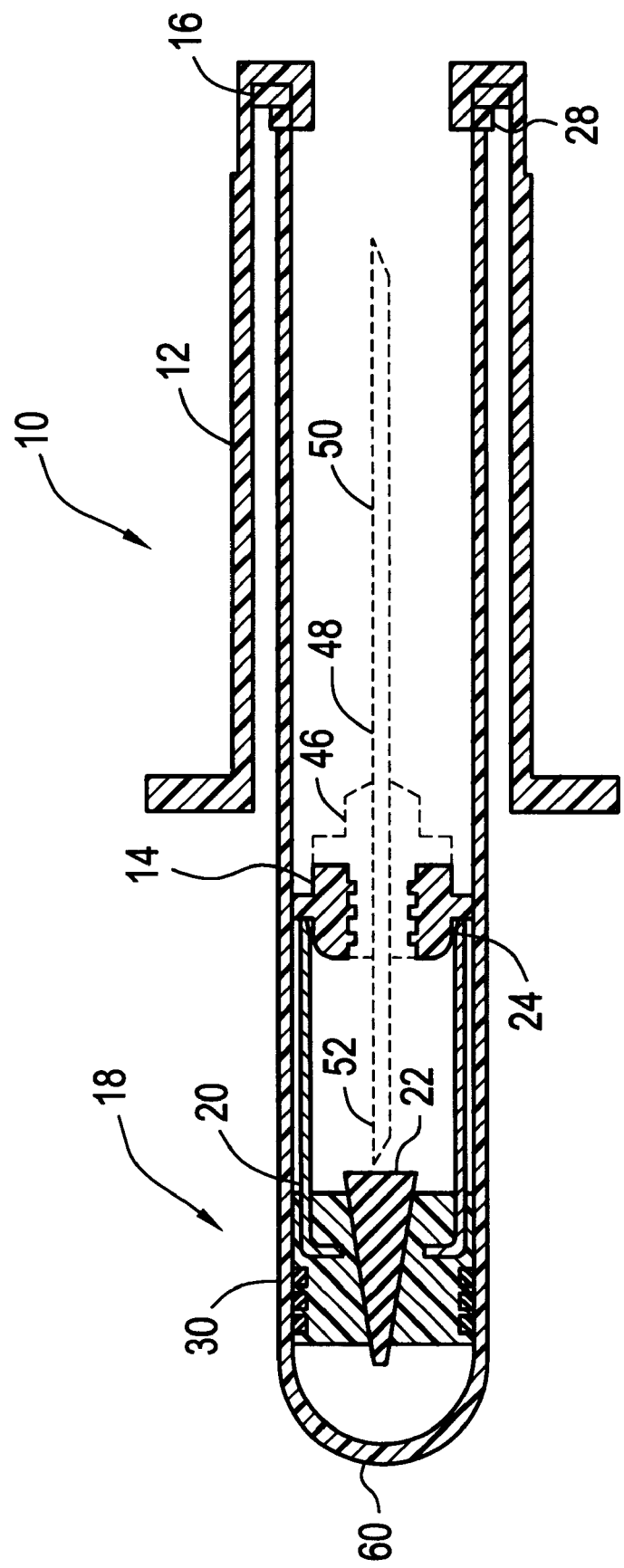
FIG. 7 is a sectional view of the disposable medical collection tube holder with the needle, detachable needle port hub and combination part fully retracted within the accessory chamber.

As best seen in FIG. 6, evacuated accessory 18 has been fully inserted into collection tube holder body 12 and a longitudinally axial force applied to closed proximal end 60. As axially extending catch ring 24 begins to mate with needle port hub 14 having affixed needle holder 46 and needle 48, hub release ring 16 is pushed off needle port hub 14 and into annular channel 42. Continued longitudinally axial force applied to proximal end 60 further secures the mating between needle port hub 14 and axially extending catch ring 24 and now pushes retaining ring 28 off combination part 20 and into annular channel 42. The release of hub release ring 16 from needle port hub 14 permits the mated complex (assembly) of needle port hub 14 and combination part 20 to move axially within tubular member 30. The release of retaining ring 28 from combination part 20 permits the mated complex of needle port hub 14 and combination part 20 to move axially within tubular member 30. With retaining ring 28 released, atmospheric pressure acting across gasket seals 26 causes the mated complex of needle port hub 14, affixed needle holder 46 and needle 48 and combination part 20 to retract into tubular member 30 to a position shown by FIG. 7, a position wherein the contaminated needle is completely encapsulated. The operator may safely dispose of the used assembly without fear of contamination from blood or other body fluids so drawn.

The construction of our disposable medical collection tube holder assembly will be readily understood from the foregoing description and it will be seen that we have provided a disposable medical collection tube holder assembly with retractable needle. Thus, our disposable medical collection tube holder assembly with retractable needle allows for safe disposal of used needles with minimal intervention of the operator being required, a one-handed compression operation that retracts and encloses the needle. Furthermore, while the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the appended claims.

What is claimed is:

1. A disposable medical collection tube holder assembly with retractable needle, comprising:

a collection tube holder body having a proximal end and a distal end with a central bore;

said distal end of said central bore of said collection tube holder receiving a detachable needle port hub adapted to receive a needle holder, with or without included needle, mountable therein;

an evacuated accessory having a tubular member with proximal and distal ends, said evacuated accessory longitudinally slidable within said central bore of said collection tube holder body, said evacuated accessory having a combination part releasably secured on said distal end of said tubular member;

said detachable needle port hub releasably secured within said distal end of said collection tube holder body, said detachable port hub longitudinally slidable within said central bore of said evacuated accessory when said detachable needle port hub is released;

said combination part sealing within said tubular member of said evacuated accessory to maintain a pressure differential between the interior of said tubular member of said evacuated accessory and the atmosphere; and, said combination part having a central bore therethrough and a pressure differential seal positioned therein, said pressure differential seal sealing said central bore of said combination part when said tubular member is evacuated, said combination part axially moveable within said tubular member when released.

2. A disposable medical collection tube holder assembly with retractable needle according to claim 1, wherein:

said detachable needle port hub is releasably secured within said collection tube holder body by a hub release ring; and, said distal end of said central bore of said collection tube holder body having an interior annular channel to receive said hub release ring.

3. A disposable medical collection tube holder assembly with retractable needle according to claim 2, wherein:

said combination part is releasably secured within said tubular member of said evacuated accessory by a retaining ring;

said combination part having a proximal end and a distal end, said distal end having a catch ring positioned thereon to mate with said detachable needle port hub of said collection tube holder body, said proximal end being fitted with a plug body;

said plug body having a central bore therethrough and a pressure differential seal positioned therein to seal said central bore of said plug body; and, said plug body sealingly engaging the interior wall of said tubular member and said pressure differential seal sealing said central bore of said plug body to maintain said pressure differential between said interior of said tubular member of said evacuated accessory and said atmosphere.

4. A disposable medical collection tube holder assembly with retractable needle according to claim 3, wherein:

said combination part of said evacuated accessory and said detachable needle port hub said collection tube holder are engaged by application of a longitudinally axial force on said evacuated accessory; and, said hub release ring of said detachable needle port and said retaining ring of said combination part are sequentially releasable by application of said longitudinally axial force on said evacuated accessory.

5. A disposable medical collection tube holder assembly with retractable needle according to claim 4, wherein:

sequentially releasing said hub release ring and said retaining ring allows differential pressure between the atmosphere and said evacuated interior of said tubular member to move said combination part with said detachable needle port hub and needle mounted therein into the interior of said tubular body.

6. A disposable medical collection tube holder assembly with retractable needle according to claim 5 wherein:

said longitudinally axial force on said tubular plunger is applied by exerting force on said closed proximal end of said evacuated accessory to move said evacuated accessory axially within said central bore of said collection tube holder body.

7. A disposable medical collection tube holder assembly with retractable needle according to claim 6 wherein:

said collection tube holder body includes an annularly disposed flange on the exterior of its proximal end to aid a user in grasping said collection tube holder body when said longitudinally axial force is applied to said evacuated accessory.

8. A disposable medical collection tube holder assembly with retractable needle according to claim 7 wherein:

said plug body is formed of a resilient rubber to allow sealing and reciprocation of said combination part within said tubular member.

9. A disposable medical collection tube holder assembly with retractable needle according to claim 8 wherein:

said pressure differential seal of said combination part is so shaped to accommodate the seal of a pressure differential between the atmoshere and the interior of said evacuated accessory.

10. A disposable medical collection tube holder with retractable needle according to claim 9 wherein:

said pressure differential seal of said combination part is moveable to a nonsealing position during evacuation of said evacuated accessory.

* * * * *